US009113781B2

(12) United States Patent
Wels et al.

(10) Patent No.: US 9,113,781 B2
(45) Date of Patent: Aug. 25, 2015

(54) METHOD AND SYSTEM FOR ON-SITE LEARNING OF LANDMARK DETECTION MODELS FOR END USER-SPECIFIC DIAGNOSTIC MEDICAL IMAGE READING (71) Applicants: Michael Wels, Bamberg (DE); Michael Kelm, Erlangen (DE); Michael Suehling, Erlangen (DE); Shaohua Kevin Zhou, Plainsboro, NJ (US)

(72) Inventors: Michael Wels, Bamberg (DE); Michael Kelm, Erlangen (DE); Michael Suehling, Erlangen (DE); Shaohua Kevin Zhou, Plainsboro, NJ (US)

(73) Assignee: Siemens Aktiengesellschaft, Munich (DE)

(*) Notice: Subject to any disclaimer, the term of this patent is extended or adjusted under 35 U.S.C. 154(b) by 175 days.

(21) Appl. No.: 13/761,263

(22) Filed: Feb. 7, 2013

(65) Prior Publication Data

US 2014/0219548 A1 Aug. 7, 2014

(51) Int. Cl.
G06K 9/00 (2006.01)
A61B 5/00 (2006.01)
A61B 6/00 (2006.01)
G06K 9/62 (2006.01)
G06F 19/00 (2011.01)

(52) U.S. Cl.
CPC ............... *A61B 5/0033* (2013.01); *A61B 6/00* (2013.01); *G06F 19/321* (2013.01); *G06K 9/6255* (2013.01); *G06K 9/00* (2013.01); *G06K 2209/05* (2013.01)

(58) Field of Classification Search
CPC ............ A61N 2005/1062; G01R 33/543; G06T 7/0042; G06T 7/0081; G06T 2207/10072; G06T 2207/10081; G06T 2207/30004; G06T 7/0012; G06T 2207/10076; A61B 2019/5238; A61B 6/032; G06K 2209/05; G06F 19/321; Y10S 128/922
USPC ......... 382/128, 129, 131, 100, 103, 106–107, 382/162, 168, 173
See application file for complete search history.

(56) References Cited

U.S. PATENT DOCUMENTS

| 7,876,938 | B2* | 1/2011 | Huang et al. ................... 382/128 |
| 8,406,494 | B2 | 3/2013 | Zhan et al. |
| 2003/0194057 | A1* | 10/2003 | Dewaele ........................ 378/210 |
| 2007/0016016 | A1* | 1/2007 | Haras et al. .................... 600/431 |
| 2007/0081712 | A1* | 4/2007 | Huang et al. ................... 382/128 |
| 2007/0237373 | A1* | 10/2007 | Kiraly et al. .................... 382/128 |
| 2008/0129321 | A1 | 6/2008 | Suzuki et al. |
| 2008/0267483 | A1* | 10/2008 | Zhan et al. ..................... 382/131 |
| 2009/0034813 | A1* | 2/2009 | Dikmen et al. ................ 382/131 |
| 2009/0067696 | A1 | 3/2009 | Bystrov et al. |
| 2009/0324012 | A1* | 12/2009 | Sun et al. ....................... 382/103 |
| 2010/0034440 | A1 | 2/2010 | Zhan et al. |
| 2010/0067764 | A1* | 3/2010 | Lu et al. ......................... 382/131 |
| 2010/0080434 | A1 | 4/2010 | Seifert et al. |

(Continued)

*Primary Examiner* — Vu Le
*Assistant Examiner* — Aklilu Woldemariam (57) ABSTRACT A method and system for on-line learning of landmark detection models for end-user specific diagnostic image reading is disclosed. A selection of a landmark to be detected in a 3D medical image is received. A current landmark detection result for the selected landmark in the 3D medical image is determined by automatically detecting the selected landmark in the 3D medical image using a stored landmark detection model corresponding to the selected landmark or by receiving a manual annotation of the selected landmark in the 3D medical image. The stored landmark detection model corresponding to the selected landmark is then updated based on the current landmark detection result for the selected landmark in the 3D medical image. The landmark selected in the 3D medical image can be a set of landmarks defining a custom view of the 3D medical image.

22 Claims, 6 Drawing Sheets (a)          (b)          (c)

(56) References Cited

U.S. PATENT DOCUMENTS

| | | | |
|---|---|---|---|
| 2010/0100560 A1* | 4/2010 | Bystrov et al. | 707/769 |
| 2010/0135546 A1* | 6/2010 | Cziria | 382/128 |
| 2010/0166283 A1* | 7/2010 | Grosskopf | 382/131 |
| 2010/0189320 A1* | 7/2010 | Dewaele | 382/128 |
| 2011/0007954 A1* | 1/2011 | Suehling et al. | 382/128 |
| 2011/0142320 A1* | 6/2011 | Gupta et al. | 382/131 |
| 2011/0182493 A1* | 7/2011 | Huber et al. | 382/132 |
| 2011/0206260 A1* | 8/2011 | Bergmans et al. | 382/131 |
| 2013/0121545 A1* | 5/2013 | Feng et al. | 382/128 |
| 2014/0093153 A1* | 4/2014 | Sofka et al. | 382/131 |

* cited by examiner

METHOD AND SYSTEM FOR ON-SITE LEARNING OF LANDMARK DETECTION MODELS FOR END USER-SPECIFIC DIAGNOSTIC MEDICAL IMAGE READING

BACKGROUND OF THE INVENTION

The present invention relates to learning of landmark detection models for landmark detection in medical images, and more particularly, to on-site learning of landmark detection models for end user-specific diagnostic medical image reading.

In radiology, routine reading of three dimensional medical images, e.g., from computed tomography (CT), magnetic resonance imaging (MRI), positron emission tomography (PET), etc., usually follows fixed rules and protocols. Such protocols are sometimes established and re-fined by individual hospitals on their own behalf to ensure and to achieve a high quality of care. Also, physicians often develop their own methodology for a systematic reading of cases. Depending on the medical question to be answered, navigation through the data sets may require the inspection of certain important anatomical landmarks, in terms of 3D coordinates, or their surroundings. Standardized tomographic 2D views, i.e., planes, in the 3D medical image data may have to be oriented in relation to such anatomical landmarks. Furthermore, semantic information about landmark locations in specific patient data sets may be used, often in combination with patient-specific information from other sources, for higher-level image post-processing like image fusion, content-based image retrieval, or knowledge-based decision support.

However, manual navigation to particular anatomical landmarks and double oblique alignment of 2D planes to the anatomical landmarks is time consuming and the radiologists' workflow can significantly be improved by automatic detection of landmarks and corresponding oriented planes. Algorithms for automatic detection of landmarks and oriented planes are typically tied to specific clinical questions and modalities. Different or newly developed radiological examinations and workflows may require different landmarks and alternatively oriented view planes in various imaging modalities and contexts. Furthermore, hospitals and groups of physicians all over the world may have their own individual preferences, leading to greater challenges in automating landmark detecting and image orientation.

BRIEF SUMMARY OF THE INVENTION

The present invention provides a method and system for automatic on-site learning of landmark detection models for end user-specific diagnostic medical image reading. Embodiments of the present invention address the problem of fully automatic 3D landmark detection, and provide a workflow individualization methodology that can cope with a dynamic radiological environment. Embodiments of the present invention allow an end user to vary scenarios of radiological image reading in terms of relevant landmarks or view planes and associated medical imaging data of the appropriate modality.

In one embodiment of the present invention, a selection of a landmark to be detected in a 3D medical image is received. A current landmark detection result for the selected landmark in the 3D medical image is determined by at least one of automatically detecting the selected landmark in the 3D medical image using a stored landmark detection model corresponding to the selected landmark and receiving a manual annotation of the selected landmark in the 3D medical image. The stored landmark detection model corresponding to the selected landmark is updated based on the current landmark detection result for the selected landmark in the 3D medical image.

These and other advantages of the invention will be apparent to those of ordinary skill in the art by reference to the following detailed description and the accompanying drawings.

DETAILED DESCRIPTION

The present invention is directed to a method and system for automatic on-site learning of landmark detection models for end user-specific diagnostic medical image reading. Embodiments of the present invention are described herein to give a visual understanding of the methods described herein. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Figure 1:
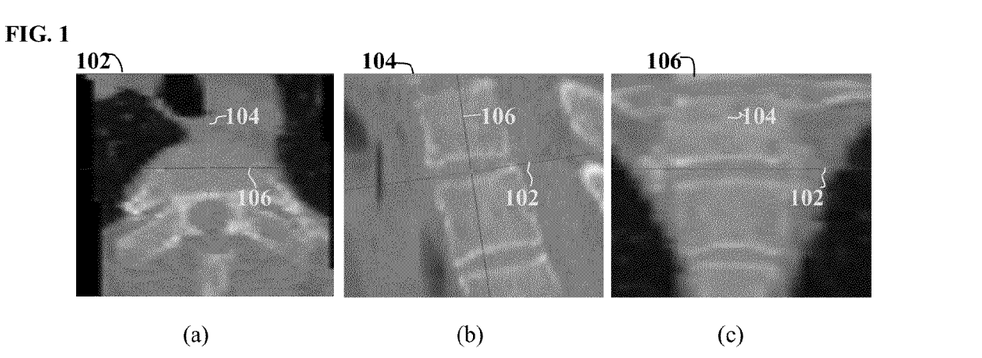
FIG. 1 illustrates 2D views of a 3D medical image volume oriented based on anatomical landmarks.

Embodiments of the present invention address the problem of fully automatic 3D landmark detection, and provide a workflow individualization methodology that can cope with a dynamic radiological environment. Embodiments of the present invention allow an end user to vary scenarios of radiological image reading in terms of relevant landmarks or view planes and associated medical imaging data of the appropriate modality. The term "landmarks", as used herein may refer to anatomical landmarks in medical imaging data, but is not restricted to anatomical entities and may also include characteristic deformations, etc. Landmarks can be represented by 3D coordinates. Three or more landmarks can be used to characterize image view/planes oriented to the landmarks. FIG. 1 illustrates 2D views of a 3D medical image volume oriented based on anatomical landmarks. As shown in FIG. 1, 2D viewing planes 102, 104, and 106 are oriented based on four anatomical landmarks associated with the spinal disk. Images (a), (b), and (c) are multi-planar reconstruction (MPR) images generated from a 3D medical imaging volume, corresponding to viewing planes 102, 104, and 106, respectively.

Providers of radiological image viewers typically offer systems for fully automatic detection of specific landmarks. However, there are several problems with such systems. For example, the software providers do not have the capabilities to handle and anticipate the huge variety of possible landmarks that clinicians may wish to detect, and the market for very special landmarks may not be big enough to be profitable. Medical research or particular clinical routines may require detection of completely new, unforeseen landmarks, that are not included in the existing systems. Also, medical images and annotations may not be permitted to leave hospitals, e.g., for training landmark detector models off-site, due to regulatory issues. Further, existing landmark detection systems may not perform as expected when applied to other or new imaging modalities (e.g., dual source CT, new MRI sequences, etc.). Embodiments of the present invention work on a database of 3D medical images and allow end users to set up and tune detector models for detecting various landmarks in the 3D medical images. Embodiments of the present invention provide a system which updates current landmark detection models based on user feedback, in the background without being noticed by the user while the system is in use. Embodiments of the present invention employ on-site landmark detection models, for which the associated data is defined locally at the site of the user and machine learning for model generation and updates are performed locally, as well.

Figure 2:
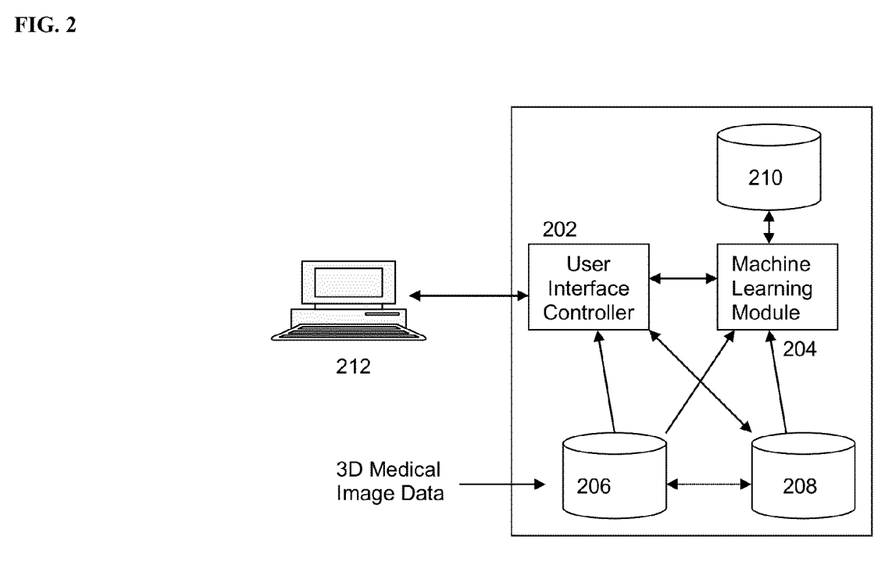
FIG. 2 illustrates an interactive 3D medical image viewing system according to an embodiment of the present invention.

FIG. 2 illustrates an interactive 3D medical image viewing system according to an embodiment of the present invention. The system 200 of FIG. 2 can be implemented on one or more computers well-known computer processors, memory units, storage devices, computer software, and other components, and provides fully automatic detection of user-defined landmarks with on-site knowledge acquisition and on-site detection model generation. Based on these landmarks, user-defined zooming factors and aligned 2D views are also provided by the system 200. As shown in FIG. 2, the system 200 includes a user interface controller 202, a machine learning module 204, a 3D medical image database 206, a landmark annotation database 208, and a detector model database 210.

The user interface controller 202 controls an interactive 3D medical image viewer to be displayed on an end user device 212 of an end user. The end user may be a radiologist that uses the interactive 3D medical image viewer for diagnostic reading of 3D medical image data. The user-interface controller 202 can retrieve 3D medical images of any imaging modality from the 3D medical image database 206 and control the display of the 3D medical images on the interactive 3D medical image viewer. In particular, the user interface controller 202 can generate 2D views from a 3D medical image and control the interactive 3D medical image viewer to display the 2D views on the end user device 212. The user interface controller 202 can automatically select 2D views based on landmarks that are detected or annotated in a 3D medical image. The user interface controller 202 can also select 2D views in response to a selection of the end user received via the interactive 3D medical image viewer on the end user device 212. The user interface controller 202 can control the interactive 3D medical image viewer to display detection results for automatically detected landmarks, and store landmark annotations entered by the end user in the landmark annotation database 208. The user interface controller can also control the machine learning module 204 to perform automatic landmark detection is response to a user selection in the interactive 3D medical image viewer invoking automatic landmark detection.

Figure 3:
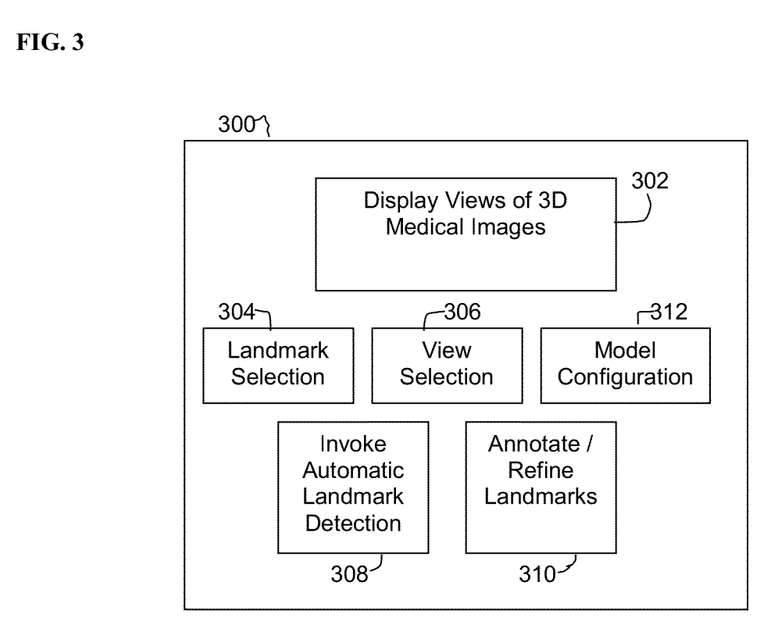
FIG. 3 illustrates a functional block diagram of the 3D medical image viewer 300 according to an embodiment of the present invention.

The interactive 3D medical image viewer is a graphical user interface displayed on a display of the end user device 212. The interactive 3D medical image viewer allows the end user to interact with the system 200 using input/output controls (e.g., display, keyboard, mouse, touch-screen, speakers, buttons, etc.) of the end-user device 212. FIG. 3 illustrates a functional block diagram of the 3D medical image viewer 300 according to an embodiment of the present invention. The block diagram of FIG. 3 represents various capabilities of the 3D medical image viewer 300, but the capabilities of the interactive 3D medical image viewer 300 are not limited to those shown in FIG. 3. As shown in FIG. 3, the interactive 3D medical image viewer 300 provides a display of views of 3D medical image data. For example, the interactive medial image viewer 300 can include windows providing various 2D views of 3D medical image data, as well as a 3D visualization of the 3D medical image data. The interactive 3D medical image viewer 300 provides a tool for manual view selection 306 for selecting 2D viewing planes. The interactive 3D medical image viewer 300 provides tools for allowing the user to select a landmark 302 and invoke automatic landmark detection 308. The interactive 3D medical image viewer 300 provides tools for manual annotation and/or refinement of landmarks 308. This allows a user to manually annotate a target landmark in 3D medical image data and refine landmarks automatically detected in 3D medical image data. The interactive 3D medical image viewer 300 also provides tools for landmark detection model configuration 310. For example, the user can define and adjust custom detection system parameters for the landmark detection models, such as a size of a context surrounding the 3D landmark to be considered. The user can also define different landmark detection models for different imaging modalities. The above described capabilities of the interactive 3D medical image viewer can be implemented using various known features of graphical user interfaces, such as buttons, drop-down menus, sliders, fields, menus, etc.

Returning to FIG. 2, the 3D medical image database 206 stores 3D medical images received by the system 200. The 3D medical images may be acquired using any imaging modality, such as computed tomography (CT), magnetic resonance imaging (MRI), positron emission tomography (PET), ultrasound, etc. The 3D medical images may be received directly image acquisition devices at a same location as the system and stored in the 3D medical image database 306 as they are acquired. The 3D medical image database 206 incrementally, as each 3D medical image viewed by the end user on the interactive 3D medical image viewer is included in the 3D medical image database 206. The 3D medical image database 206 can organize the 3D medical images based on imaging modality, landmark to be detected in the image, medical issue associated with the patient, and/or other patient information (e.g., age, gender, etc.), but the present invention is not limited thereto.

The landmark annotation database 208 stores landmark annotations associated with 3D medical images. The landmark annotations can be generated by an end-user manually annotating a landmark using the interactive 3D medical image viewer or can be generated by automatic landmark detection by the machine learning module 204. Once a landmark is automatically detected using a trained detection model, a user can be given the option to accept the landmark detection result, and if accepted by the user, the landmark detection result is stored as a landmark annotation in the landmark annotation database 208. If the user does not accept the automatically detected landmark, the user may refine the detection result, and then the defined landmark detection result can be stored as a landmark annotation in the landmark annotation database 208. Accordingly, the landmark annotation database 208 is incrementally updated based on landmark detection results. The landmark annotation database may be organized based on type of landmark and/or imaging modality, but the present invention is not limited thereto. The landmark annotation database 208 and the 3D medical image database 206 are linked to each other such that each the landmark annotation in the landmark annotation database 208 is linked to the corresponding 3D medical image in which the landmark was annotated/detected in the 3D medical image database 206.

The machine learning module 204 performs machine learning to train detection models for 3D object position detection. In an embodiment of the present invention, the detection model for a particular landmark is a 3D translation detector trained with Haar-like features to detect the position of a 3D bounding box centered at the landmark position. The machine learning module trains detection modules for a particular landmark using the landmark annotations for that landmark stored in the landmark annotation database 208, as well as the corresponding 3D medical images in the 3D medical image database 206 that are linked to the landmark annotations. In particular, the machine learning module 204 uses the landmark annotations as positive training samples, selects negative training samples from non-landmark regions in the corresponding 3D medical images, and trains the landmark detection model based on features extracted from the positive and negative training samples. In a possible implementation, the machine learning module 204 trains a random-forest classifier for each landmark detection module. In another possible implementation, the machine learning module 204 trains a probabilistic boosting tree (PBT) classifier for each landmark detection model. It is to be understood that the present invention is not limited to any particular type of landmark detection model, and any type of machine learning classifier can be used to train the landmark detection models. In another possible implementation, the user can be given a choice of classifier types to use to train the landmark detection model for each landmark, and the user can select from the provided classifier types using the interactive 3D medical image viewer.

The detector model database 210 stores the landmark detection models trained by the machine learning module 204. When automatic landmark detection is requested for a particular landmark, the machine learning module 204 retrieves the trained landmark detection model for that landmark from the detector model database 210 and automatically detects the landmark in a 3D medical image using the trained landmark detection model.

The machine learning module 204 has on-line learning capability to automatically update landmark detection models stored in the detector model database 210 based on a new landmark annotations that are stored in the landmark annotation database 208. In particular, after a particular type of landmark manually annotated in a 3D medical image by a user or automatically detected by the machine learning module 204 and accepted by a user (possible after refinement by the user), the annotated/detected landmark is stored as a new landmark annotation in the landmark annotation database 208 and the machine learning module 204 updates the landmark detection model for that type of landmark to include the new landmark annotation as well as negative training samples selected from the corresponding 3D medical image.

In an advantageous implementation, the incremental landmark detection model updates can be implemented using On-line Random Forests, which can quickly update a random forest classifier trained for a particular landmark. The machine learning module 204 performs on-site model updates in the background while a user can still interact with the interactive 3D medical image viewer to diagnostically read a current 3D medical image. In particular, the machine learning module 204 performs operations such as pre-processing of the medical image data (e.g., re-sampling to a unified resolution), initial landmark detection model generation, and/or updating or re-training of existing landmark detection models as background operations while the end user interacts with the interactive 3D medical image viewer controller by the user interface controller 202.

In a possible embodiment, the system 200 of FIG. 2 may be implemented on one or more servers, and communicate with the end user device 212 and other end user device as client devices. In another possible embodiment, the system 200 may be implemented on the same end user device 212 on which the interactive 3D medical image viewer is displayed.

Figure 4:
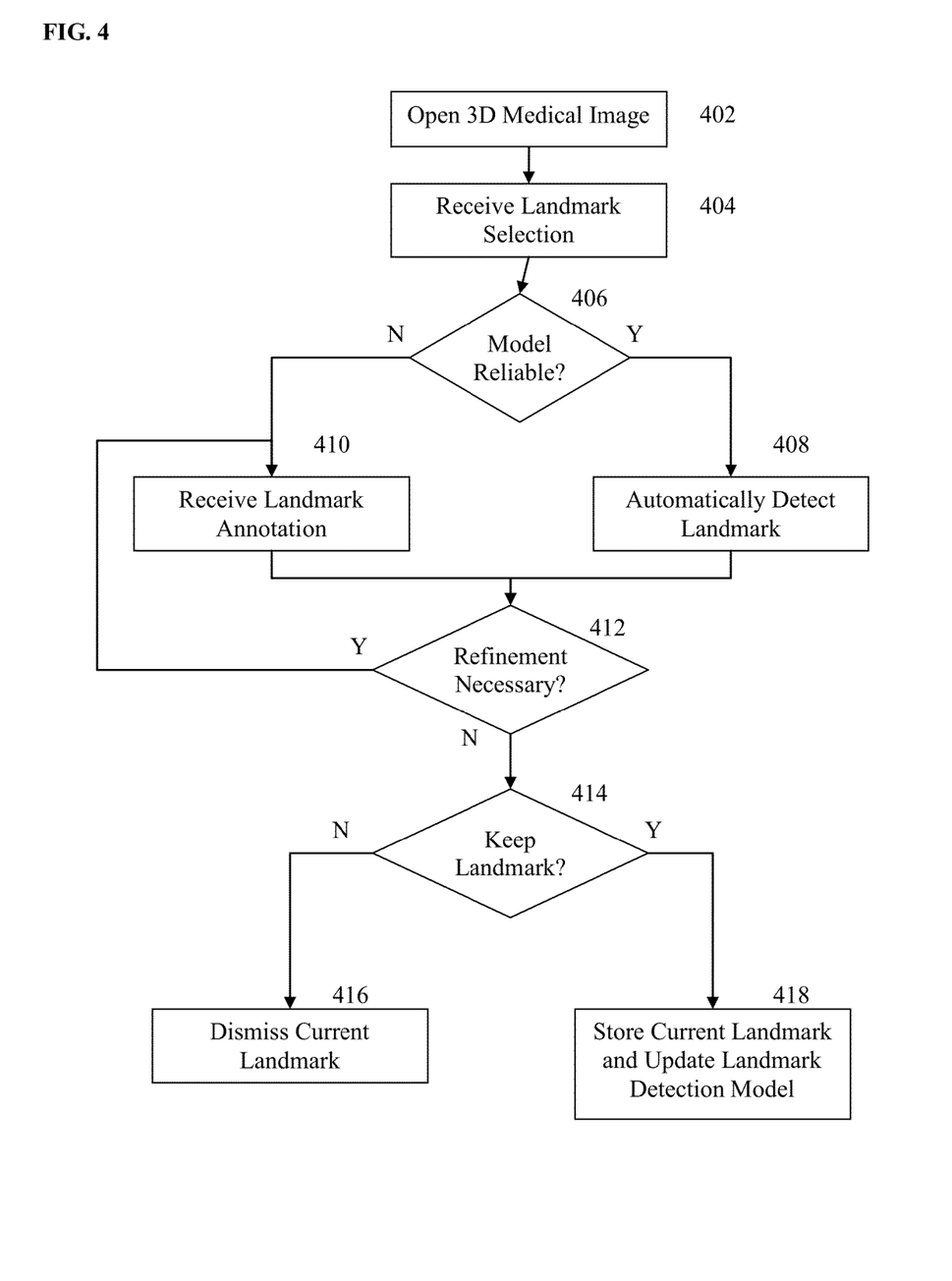
FIG. 4 illustrates a method of on-site learning of a landmark detection model according to an embodiment of the present invention.

FIG. 4 illustrates a method of on-site learning of a landmark detection model according to an embodiment of the present invention. As illustrated in FIG. 4, at step 402, a 3D medical image is opened. For example, the user interface controller 202 can retrieve a 3D medical image volume from the 3D medical image database 206 and control the interactive 3D medical image viewer to display the 3D medical image volume on the end-user device 212. The 3D medical image can be an image frame any type of medical imaging modality.

At step 404, a landmark selection is received from the end user via the interactive 3D medical image viewer. The landmark selection corresponds to the type or name of the landmark to be detected in the 3D medical image. For example, the end user can select from a drop down menu or the like providing a list of possible landmarks. It is also possible that multiple options corresponding to multiple detection models having different configurations can be available for a particular type of landmark. If the type of landmark the end user wants to detect is not provided in the list of possible landmarks, the end user can enter a new landmark type or name as the landmark selection. As described above, a custom view can be defined by viewing planes oriented to three or more landmarks. Accordingly, in a possible embodiment the landmark selection can be a selection of a particular view (either new or previously defined), and the view can define a set of landmarks to be detected.

At step 406, it is determined if a landmark detection model for the selected landmark is reliable. In a possible embodiment a confidence score can be associated with each landmark detection model stored in the detector model database 210. For example, the confidence associated with a particular landmark detection model can be determined by a number of samples used in training the landmark detection model, user feedback of reliability of previous landmark detection results using the model, detection error in a test image, or some combination of the above reliability measures. It is determined that the landmark detection model for the selected landmark is not reliable if no landmark detection model currently exists for the selected landmark. If it is determined that the landmark detection model is reliable, the method proceeds to step 408. If it is determined that the landmark detection model is no reliable, the method proceeds to step 410.

At step 408, the selected landmark is automatically detected in the 3D medical image using the trained landmark detection model corresponding to the selected landmark. In particular, the machine learning module 204 automatically detects the landmark using the landmark detection model stored in the detector model database 210 for that landmark, and the user interface model 202 controls the interactive 3D medical image viewer to display the landmark detection results on the display of the end user device 212. Once the landmark is automatically detected at step 408, the method proceeds to step 412.

At step 410, a landmark annotation for the selected landmark is received via the interactive 3D medical image viewer. The landmark annotation is a manual annotation of the landmark in the 3D medical image displayed in the interactive 3D medical image viewer. The annotation tool provided in the interactive 3D medical image viewer can be used by the end user to enter the landmark annotation. Once the landmark annotation is received at step 410, the method proceeds to step 412.

At step 412, it is determined whether refinement of the current landmark is necessary. In an exemplary implementation the current landmark (the landmark detection result of step 408 or the landmark annotation result of step 410) is displayed to the end user in the interactive 3D medical image viewer and an a user input is received indicating whether refinement of the current landmark is necessary. If it is determined that refinement of the current landmark is necessary, the method returns to step 410. In this case a landmark annotation of the user received at step 410 corresponds to a refinement of the current landmark detection/annotation result. If it is determined that no refinement of the current landmark is necessary, the method proceeds to step 414.

At step 414, it is determined if the current landmark should be kept. In an exemplary implementation, the determination of whether to keep the current landmark can depend on user input received via the interactive 3D medical image viewer. In this case, the user input may be received in response to providing the end user an option to keep or dismiss the current landmark. If it is determined that the current landmark should not be kept, the method proceeds to step 416. If it is determined that the current landmark should be kept, the method proceeds to step 418.

At step 416, the current landmark is dismissed. In particular, the current landmark detection or annotation result is not stored as a landmark annotation in the landmark annotation database 208.

At step 418, the current landmark is stored and the landmark detection model corresponding to the current landmark is updated. In particular, the current landmark detection or annotation result is stored as a new landmark annotation in the landmark annotation database 208. The machine learning module 204 then updates the landmark detection module corresponding stored in the detector model database 210 based on the new landmark annotation stored in the landmark annotation database 208. The machine learning module can also update a confidence associated with the landmark detection model corresponding to the landmark. If no detection model exists for the landmark in the detector model database 210, the machine learning module 204 can generate an initial landmark detection model based in part on the new landmark annotation and store the landmark detection model in the detector model database 210. In an advantageous implementation, the above describe operations for updating the landmark detection model corresponding to the landmark are performed by the machine learning module 204 as background operations while the end user can continue to interact with the interactive 3D medical image viewer.

As zoom factors and aligned views can be represented by a number of landmarks, managing customized "views", which represent a higher level of graphical user interface abstraction, can also be supported by the system. In a possible implementation, if the system described herein is combined with existing landmark detection algorithms for specific landmarks and specific imaging modalities, pre-stored existing landmark detection modules can be relied on for automated landmark detection until a critical amount of new data and annotations are received to fully support newly defined zoom factors and 2D aligned views. This will make the system less sensitive to detection errors in the early phase of using new detection models.

Examples of scenarios in which the system and method described above can be implemented include: detection of certain landmarks in neuroradiology that are required to spatially normalize brain MR scans to the Talairach stereotaxic atlas; aligning a field-of-view with the blood flow direction perpendicular to the aortic and mitral valves for aortic and mitral valve assessment; aligning views with the vertebral disks and/or bodies for improved reading of abdominal CT scans; and fully automatic localization of the nipple to speed up the clinical workflow in breast cancer diagnostics, where suspicious lesions are described, among other things, by their distance to the nipple. It is to be understood that the above examples are in now way intended to limit the present invention, and embodiments of the present invention may be applied to any type of landmark in any imaging modality.

Figure 5:
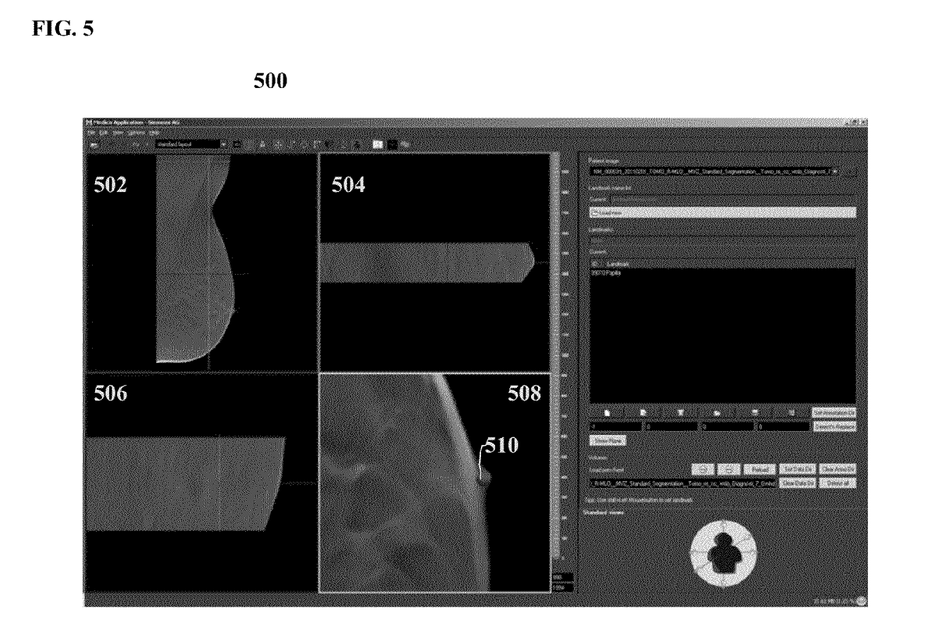
FIG. 5 illustrates an exemplary graphical user interface of an interactive 3D medical image viewer displayed on an end user device.

FIG. 5 illustrates an exemplary graphical user interface of an interactive 3D medical image viewer displayed on an end user device. As shown in FIG. 5, the graphical user interface 500 shows 2D views 502, 504, and 506, and a zoomed in view 508 of a 3D digital breast tomosynthesis image, as well as an annotated landmark 510 corresponding to the nipple.

Figure 6:
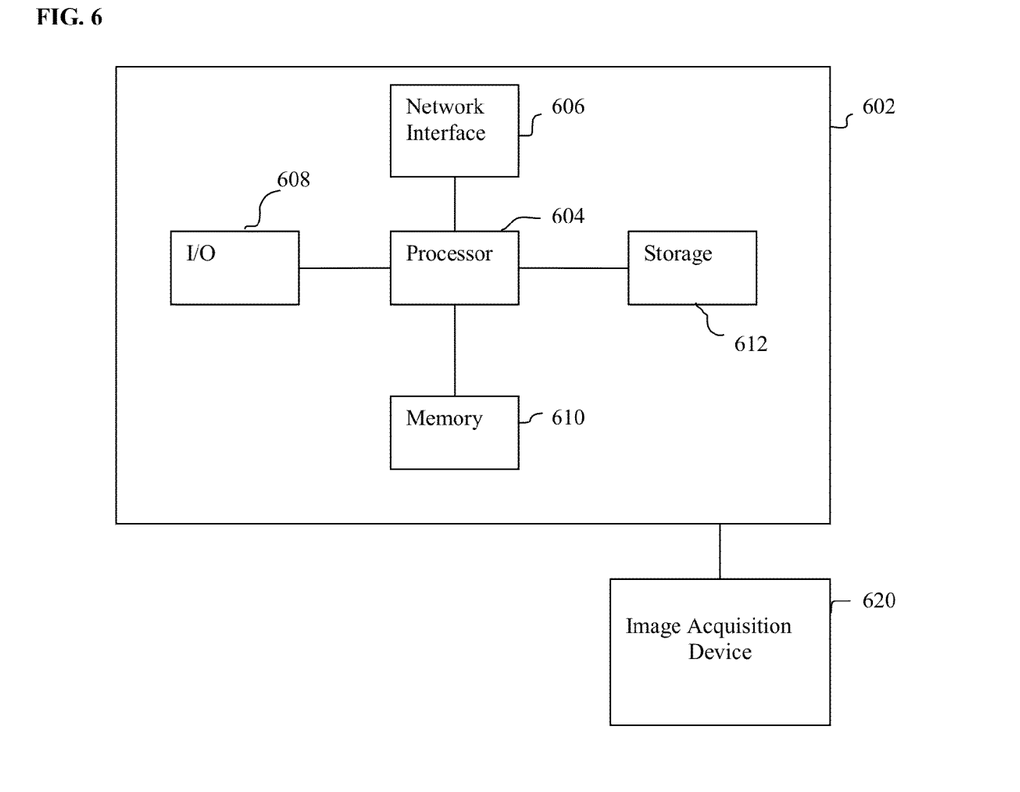
FIG. 6 is a high level block diagram of a computer capable of implementing the present invention.

The above-described methods for on-site learning of landmark detection models and automatic landmark detection, as well as the system and end user device of FIG. 2, may be implemented on a computer using well-known computer processors, memory units, storage devices, computer software, and other components. A high level block diagram of such a computer is illustrated in FIG. 6. Computer 602 contains a processor 604 which controls the overall operation of the computer 602 by executing computer program instructions which define such operations. The computer program instructions may be stored in a storage device 612, or other computer readable medium (e.g., magnetic disk, CD ROM, etc.) and loaded into memory 610 when execution of the computer program instructions is desired. Thus, the steps of the method of FIGS. 4 may be defined by the computer program instructions stored in the memory 610 and/or storage 612 and controlled by the processor 604 executing the computer program instructions. An image acquisition device 620, such as a CT scanning device, MR scanning device, etc., can be connected to the computer 602 to input medical images to the computer 602. It is possible to implement the image acquisition device 620 and the computer 602 as one device. It is also possible that the image acquisition device 620 and the computer 602 communicate wirelessly through a network. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for on-line learning of landmark detection models comprising:

receiving a selection of a landmark to be detected in a 3D medical image;

determining a current landmark detection result for the selected landmark in the 3D medical image by:

automatically determining, by a processor, whether a stored trained machine-learning based landmark detection model corresponding to the selected landmark is reliable, in response to a determination that the stored trained machine-learning based landmark detection model corresponding to the selected landmark is reliable, automatically detecting the selected landmark in the 3D medical image using the stored trained machine-learning based landmark detection model corresponding to the selected landmark, and in response to a determination that the stored trained machine-learning based landmark detection model corresponding to the selected landmark model is not reliable, receiving a manual annotation of the selected landmark in the 3D medical image; and updating the stored trained machine-learning based landmark detection model corresponding to the selected landmark based on the current landmark detection result for the selected landmark in the 3D medical image.

2. The method of claim 1, wherein automatically determining, by a processor, whether the stored trained machine-learning based landmark detection model corresponding to the selected landmark is reliable comprises:

determining that the stored trained machine-learning based landmark detection model corresponding to the selected landmark is not reliable when it is determined that no stored landmark detection model corresponding to the selected landmark exists.

3. The method of claim 1, wherein automatically determining, by a processor, whether the stored trained machine-learning based landmark detection model corresponding to the selected landmark is reliable comprises:

determining whether the stored trained machine-learning based landmark detection model corresponding to the selected landmark is reliable based on a confidence value associated with the stored trained machine-learning based landmark detection model corresponding to the selected landmark, wherein the confidence value is based on at least one of:

a number of training samples used to train the stored trained machine-learning based landmark detection model corresponding to the selected landmark, user input related to previous landmark detection results using the stored trained machine-learning based landmark detection model corresponding to the selected landmark, or detection error of the stored trained machine-learning based landmark detection model corresponding to the selected landmark in a test image.

4. The method of claim 1, further comprising:

prior to updating the stored trained machine-learning based landmark detection model, determining whether the current landmark detection result needs to be refined; and in response to a determination that the current landmark detection result needs to be refined, receiving a manual annotation refining the current landmark detection result.

5. The method of claim 1, wherein updating the stored trained machine-learning based landmark detection model corresponding to the selected landmark based on the current landmark detection result for the selected landmark in the 3D medical image comprises:

storing the current landmark detection result for the selected landmark as a new landmark annotation in a database of landmark annotations; and updating the stored trained machine-learning based landmark detection model corresponding to the selected landmark in response to the storing of the new landmark annotation in the database of landmark annotations.

6. The method of claim 5, wherein storing the current landmark detection result for the selected landmark as a new landmark annotation in a database of landmark annotations comprises:

storing the current landmark detection result for the selected landmark as the new landmark annotation in a database of landmark annotations in response to a user input to keep the current landmark detection results.

7. The method of claim 5, wherein updating the stored trained machine-learning based landmark detection model corresponding to the selected landmark based on the current landmark detection result for the selected landmark in the 3D medical image further comprises:

linking the new landmark annotation in the database of landmark annotations with the 3D medical image stored in a database of medical images.

8. The method of claim 7, wherein updating the stored trained machine-learning based landmark detection model corresponding to the selected landmark in response to the storing of the new landmark annotation in the database of landmark annotations comprises:

adding the new landmark annotation to a set of positive training samples corresponding to the selected landmark;

adding negative training samples selected from the 3D medical image linked to the new landmark annotation to a set of negative training samples corresponding to the selected landmark; and updating the stored trained machine-learning based landmark detection model corresponding to the selected landmark based on the set of positive training samples corresponding to the selected landmark and the set of negative training samples corresponding to the selected landmark.

9. The method of claim 1, wherein updating the stored trained machine-learning based landmark detection model corresponding to the selected landmark based on the current landmark detection result for the selected landmark in the 3D medical image comprises:

updating the stored trained machine-learning based landmark detection model corresponding to the selected landmark based on the current landmark detection result using on-line Random Forests.

10. The method of claim 1, wherein the selected landmark comprises a plurality of landmarks defining a custom view of the 3D medical image.

11. An apparatus for interactive viewing of 3D medical images and on-line learning of landmark detection models comprising:
- a 3D medical image database to store 3D medical images;
- a landmark annotation database to store landmark annotations of a plurality of landmarks;
- a detection model database to store trained machine-learning based landmark detection models corresponding to a plurality of landmarks;
- a user interface controller configured to control an interactive 3D medical image viewer including a plurality of display windows to display a plurality of views of a 3D medical image stored in the 3D medical image database, a user control for manually annotating a landmark in the 3D medical image, and a user control for invoking automatic landmark detection in the 3D medical image, and configured to control the landmark annotation database to store a manually annotated or automatically detected landmark in the 3D medical image as a landmark annotation; and
- a machine learning module configured to perform automatic landmark detection of a selected landmark in the 3D medical image displayed on the interactive 3D medical image viewer using a corresponding trained landmark detection model stored in the detection model database, and configured to incrementally update the corresponding trained detection model stored in the detector model database in response a manually annotated or automatically detected landmark in the 3D medical image being stored in the landmark annotations database as a landmark annotation corresponding to the selected landmark.

12. The apparatus of claim 11, wherein the user interface controller is further configured to control the interactive 3D medical image viewer to display an automatic landmark detection result in response to the machine learning module automatically detecting a selected landmark in the 3D medical image displayed on the interactive 3D medical image viewer.

13. The apparatus of claim 11, wherein the landmark annotations stored in the landmark annotations database are linked to corresponding 3D medical images stored in the 3D medical image database.

14. A non-transitory computer readable medium storing computer program instructions for on-line learning of landmark detection models, the computer program instructions when executed by a processor cause the processor to perform operations comprising:
- receiving a selection of a landmark to be detected in a 3D medical image;
- determining a current landmark detection result for the selected landmark in the 3D medical image by:
  - automatically determining, by a processor, whether a stored trained machine-learning based landmark detection model corresponding to the selected landmark is reliable,
  - in response to a determination that the stored trained machine-learning based landmark detection model corresponding to the selected landmark is reliable, automatically detecting the selected landmark in the 3D medical image using the stored trained machine-learning based landmark detection model corresponding to the selected landmark, and
  - in response to a determination that the stored trained machine-learning based landmark detection model corresponding to the selected landmark model is not reliable, receiving a manual annotation of the selected landmark in the 3D medical image; and
- updating the stored trained machine-learning based landmark detection model corresponding to the selected landmark based on the current landmark detection result for the selected landmark in the 3D medical image.

15. The non-transitory computer readable medium of claim 14, wherein automatically determining whether the stored trained machine-learning based landmark detection model corresponding to the selected landmark is reliable comprises:
- determining whether the stored trained machine-learning based landmark detection model corresponding to the selected landmark is reliable based on a confidence value associated with the stored trained machine-learning based landmark detection model corresponding to the selected landmark, wherein the confidence value is based on at least one of:
- a number of training samples used to train the stored trained machine-learning based landmark detection model corresponding to the selected landmark,
- user input related to previous landmark detection results using the stored trained machine-learning based landmark detection model corresponding to the selected landmark, or
- detection error of the stored trained machine-learning based landmark detection model corresponding to the selected landmark in a test image.

16. The non-transitory computer readable medium of claim 14, the operations further comprising:
- prior to updating the stored trained machine-learning based landmark detection model, determining whether the current landmark detection result needs to be refined; and
- in response to a determination that the current landmark detection result needs to be refined, receiving a manual annotation refining the current landmark detection result.

17. The non-transitory computer readable medium of claim 14, wherein updating the stored trained machine-learning based landmark detection model corresponding to the selected landmark based on the current landmark detection result for the selected landmark in the 3D medical image comprises:
- storing the current landmark detection result for the selected landmark as a new landmark annotation in a database of landmark annotations; and
- updating the stored trained machine-learning based landmark detection model corresponding to the selected landmark in response to the storing of the new landmark annotation in the database of landmark annotations.

18. The non-transitory computer readable medium of claim 17, wherein storing the current landmark detection result for the selected landmark as a new landmark annotation in a database of landmark annotations comprises:
- storing the current landmark detection result for the selected landmark as the new landmark annotation in a database of landmark annotations in response to a user input to keep the current landmark detection results.

19. The non-transitory computer readable medium of claim 17, wherein updating the stored trained machine-learning based landmark detection model corresponding to the selected landmark based on the current landmark detection result for the selected landmark in the 3D medical image further comprises:
- linking the new landmark annotation in the database of landmark annotations with the 3D medical image stored in a database of medical images.

20. The non-transitory computer readable medium of claim 19, wherein updating the stored trained machine-learning based landmark detection model corresponding to the selected landmark in response to the storing of the new landmark annotation in the database of landmark annotations comprises:
- adding the new landmark annotation to a set of positive training samples corresponding to the selected landmark;
- adding negative training samples selected from the 3D medical image linked to the new landmark annotation to a set of negative training samples corresponding to the selected landmark; and
- updating the stored trained machine-learning based landmark detection model corresponding to the selected landmark based on the set of positive training samples corresponding to the selected landmark and the set of negative training samples corresponding to the selected landmark.

21. The non-transitory computer readable medium of claim 14, wherein updating the stored trained machine-learning based landmark detection model corresponding to the selected landmark based on the current landmark detection result for the selected landmark in the 3D medical image comprises:
- updating the stored trained machine-learning based landmark detection model corresponding to the selected landmark based on the current landmark detection result using on-line Random Forests.

22. The non-transitory computer readable medium of claim 14, wherein the selected landmark comprises a plurality of landmarks defining a custom view of the 3D medical image.

* * * * *